US011135337B2

United States Patent
Lima Júnior et al.

(10) Patent No.: US 11,135,337 B2
(45) Date of Patent: Oct. 5, 2021

(54) TILAPIA SKIN PROCESSING METHOD AND USE THEREOF FOR COVERING SKIN INJURIES

(71) Applicants: COMPANHIA ENERGÉTICA DO CEARÁ—COELCE, Fortaleza (BR); INSTITUTO DE APOIO AO QUEIMADO-IAQ, Fortaleza (BR); Edmar Maciel Lima Júnior, Fortaleza (BR); Manoel Odorico de Moraes Filho, Fortaleza (BR); Marcelo José Borges de Miranda, Recife (BR); Nelson Sarto Piccolo, Goiânia (BR)

(72) Inventors: Edmar Maciel Lima Júnior, Fortaleza (BR); Manoel Odorico de Moraes Filho, Fortaleza (BR); Marcelo José Borges de Miranda, Recife (BR); Nelson Sarto Piccolo, Goiânia (BR)

(73) Assignees: COMPANHIA ENERGÉTICA DO CEARÁ (COELCE), Fortaleza (BR); Edmar Maciel Lima Júnior, Fortaleza (BR); Marcelo José Borges de Miranda, Recife (BR); UNIVERSIDADE FEDERAL DO CEARÁ (UFC), Fortaleza (BR)

( * ) Notice: Subject to any disclaimer, the term of this patent is extended or adjusted under 35 U.S.C. 154(b) by 417 days.

(21) Appl. No.: 15/757,244

(22) PCT Filed: Sep. 2, 2016

(86) PCT No.: PCT/BR2016/000084
§ 371 (c)(1),
(2) Date: Mar. 2, 2018

(87) PCT Pub. No.: WO2017/035615
PCT Pub. Date: Mar. 9, 2017

(65) Prior Publication Data
US 2018/0272026 A1    Sep. 27, 2018

(30) Foreign Application Priority Data

Sep. 3, 2015    (BR) .................. 10 2015 021435-9

(51) Int. Cl.
| | | |
|---|---|---|
| *A61L 15/40* | (2006.01) |
| *A01N 1/02* | (2006.01) |
| *A61L 15/44* | (2006.01) |
| *A61L 15/46* | (2006.01) |
| *A01N 47/44* | (2006.01) |
| *A01N 1/00* | (2006.01) |

(52) U.S. Cl.
CPC ............... *A61L 15/40* (2013.01); *A01N 1/00* (2013.01); *A01N 1/0215* (2013.01); *A01N 47/44* (2013.01); *A61L 15/44* (2013.01); *A61L 15/46* (2013.01); *A61L 2400/04* (2013.01)

(58) Field of Classification Search
None
See application file for complete search history.

(56) References Cited

U.S. PATENT DOCUMENTS

| 2013/0337227 A1 | 12/2013 | Tanaka et al. |
| 2014/0044948 A1 | 2/2014 | Tanaka et al. |

FOREIGN PATENT DOCUMENTS

| CN | 1068703 A | * | 2/1993 |
| CN | 1096458 A | | 12/1994 |
| CN | 1159482 A | | 9/1997 |
| EP | 0753313 A1 | | 1/1997 |
| WO | WO-2011042794 A2 | | 4/2011 |
| WO | WO-2013144727 A2 | | 10/2013 |

OTHER PUBLICATIONS

English translation of CN 1096458 A—1994.*
International Search Report (in English and Portuguese) and Written Opinion (in Portuguese) issued in PCT/BR2016/000084, dated Nov. 16, 2016; ISA/BR.
Alves, A. P. N. N. et al., "Avaliação microscópica, estudo histoquímico e análise de propriedades tensiométricas da pele de tilápia do Nilo," Rev Bras Queimaduras. Dezembro 2015. vol. 14, No. 3, pp. 203-210. ISSN 1982-1883. Alves, A. P. N. N. et al., "Microscopic evaluation, histochemical study and analysis of tensiometric properties of the Nile Tilapia skin," Rev Bras Queimaduras. Dec. 2015. vol. 14, No. 3, pp. 203-210. ISSN 1982-1883.
Souza, M. L. R. & Santos, H. S. L., "Análise morfológica da pele de tilápia do Nilo, (Oreochromis niloticus) através da microscópica e luz", Rev. Unimar. 1997. vol. 19. No. 3, páginas 881-8, ISSN 0100-9354. Souza, M. L. R. & Santos, H. S. L., "Morphological Analysis of the Skin of the Nile Tilapia (Oreochromis niloticus) by Light Microscope," Rev. Unimar. 1997. vol. 19. No. 3, pp. 881-888, ISSN 0100-9354.

* cited by examiner

*Primary Examiner* — Susan Hoffman
(74) *Attorney, Agent, or Firm* — Harness, Dickey & Pierce, P.L.C.

(57) ABSTRACT

The present innovation relates to the use of Tilapia skin, processed in several steps, on the basis of glycerol in concentrations ranging from 50% to 99% in a Type 5 and 7 Clean Room environments and, in certain cases, when the microbial count is high, it is necessary to have supplementary radio-sterilization with Gamma Irradiation. The skin can be used as an occlusive biological dressing in skin injuries, such as burns and acute or chronic wounds.

4 Claims, No Drawings

TILAPIA SKIN PROCESSING METHOD AND USE THEREOF FOR COVERING SKIN INJURIES

CROSS REFERENCE TO RELATED APPLICATIONS

This application is a 371 U.S. National Stage of International Application No. PCT/BR2016/000084, filed Sep. 2, 2016 and published in Portuguese as WO 2017/035615 A1 on Mar. 9, 2017. This application claims the benefit of Brazilian Application No. BR 102015021435-9, filed on Sep. 3, 2015. The disclosure of each of the above-identified applications is incorporated by reference as if set forth in their entirety herein.

TECHNICAL FIELD

The innovation refers to the use of Tilapia skin, processed in several steps, on the basis of glycerol, in concentrations ranging from 50% to 99% in Type 5 and 7 Clean Room environments and, in some cases, when the microbial count is high, it is necessary to have supplementary radio-sterilization by Gamma Irradiation. The skin can be used in burns and acute or chronic wounds, which consists of its application on the surface of injuries resulting from 2nd degree burns, whether superficial or deep, in acute wounds such as donor skin areas for autografting, or chronic, in their final stages of performing simple dressings, surgical cleaning, surgical debridements under anesthesia and skin autografting, frequently present in these injuries.

PRIOR ART

Currently, medicine in Brazil does not have any alternative for temporary heterologous skin cover (of animal origin), as part of the treatment of burns and wounds. In developed countries, especially in the United States of America, industrialized Swine Skin is used for this purpose and in a large scale for several decades. Importing this product for Brazil has never been commercially viable, considering its high cost and the economic reality of the country.

DETAILED DESCRIPTION OF THE INVENTION

The present invention describes the use of the skin of Tilapia in the surface treatment of skin injuries, such as burns, chronic wounds, among others, being obtained from fish farms, that use culture systems (tanks-net), passing through a sterilization process, as described below.

After slaughtering, tilapia skins (weighing between 800 and 1000 g) will be removed with a turquoise (tool) and washed in running water, to remove any trace of blood and other impurities and placed in sterile saline (0.9% NaCl solution), previously cooled to 4° C., for final cleaning. Then, the muscle excesses, which remain attached to the skin, will be removed and cut into 10.0 cm×5.0 cm pieces, washed with saline, following the following sterilization steps.

Step 1—the skins are placed in a sterile container containing 2% chlorhexidine gluconate (solution with surfactants), where they will remain for 30 min.

Step 2—after the previous operation, the skins will be washed with sterile saline and removed to another container containing another 2% chlorhexidine gluconate solution, where they will remain for 30 minutes.

Step 3—the skins shall be rinsed in sterile saline and placed in a container containing solution with 50% glycerol, 49% saline and 1% solution with penicillin, streptomycin and fungisol and packaged for transport (Jaguaribara-NPDNI) in an isothermal box containing ice.

The next steps will be performed in the NPDM of UFC, in a sterile environment, with horizontal or vertical laminar flow.

Step 4—Before 24 hours, the skins should be removed from the previous solution, washed with sterile saline and placed in a sterile, hermetically sealed container containing 75% glycerol, 24% saline and 1% solution with penicillin, streptomycin and fungisol in which skins are massaged for 5 minutes in this solution and held for 3 hours in a water bath (centrifuge), with a stirrer at a constant speed of 15 revolutions per minute and a temperature of 37° C.

Step 5—the skins will be removed, washed with sterile saline again and placed in another sterile and hermetic container containing 99% glycerol, 1% solution with penicillin, streptomycin and fungisol, with massage of the skins for 5 minutes in this solution and kept in water bath in a centrifuge at a temperature of 37° C. and 15 revolutions per minute for more 3 hours.

Step 6—At the end of the last step of the glycerol, the skins will be packaged in sterile double plastic envelopes and stored at 4° C. for later use, with a shelf life of up to two years.

Seven microbiological tests will be performed for gram positive, gram negative bacteria and fungi, starting in the in natura skin, i.e. before the first step and in the six steps described above. When Bioburden levels, used for bacterial counts, i.e. Bioburden Microbiological Analysis, or Microbial Limit Test, which is performed on pharmaceuticals and medical products that require control of microbial levels during processing and handling, are within the acceptable limits, the skin will be available for use.

When the skins are used, they will be removed from the envelope and washed three times in different solutions of sterile saline for five minutes each step. After this procedure, the skins will be cut to the size of the wound and applied as an occlusive dressing.

If the bacterial count is above 10/3, a supplementary sterilization step, described below, should be introduced:

Step 7—supplementary radio-sterilization, Gamma—Cobalt 60, with load dosages ranging from 15 to 50 Kilograys, depending on the Bioburden levels (microbial count).

The skin of the tilapia, when interacting with these injuries, promotes the acceleration of the healing and repair processes of the dermal matrix (due to the action of Type I Collagen in its histological structure), by adhering to the wound bed, avoiding retention of exudates and fluid loss, promoting a barrier to bacterial invasion and providing pain relief.

The invention claimed is:

1. A method of treatment of skin injuries, burns, acute wounds or chronic wounds comprising applying tilapia skin as an occlusive dressing to the skin injuries, burns, acute wounds, or chronic wounds, wherein the tilapia skin is produced by a process comprising the following steps:

removing the tilapia skins with a tool and rinsing in running water, placing the tilapia skins in a 0.9% NaCl sterile saline solution cooled to 4° C. for cleaning, removing muscle from the tilapia skins, cutting the tilapia skins into pieces, washing with saline, and sterilizing the tilapia skin using the following steps:

placing the tilapia skins in a sterile container containing about 2% chlorhexidine gluconate solution with surfactant for about 30 minutes;

washing the tilapia skins with a sterile solution and placing the tilapia skins in another container containing about 2% chlorhexidine gluconate solution for 30 minutes;

rinsing the tilapia skins with a sterile solution and placing the skins in a container containing a solution with at least 50% glycerol, saline, and 1% of a solution containing penicillin, streptomycin, and a fungicide composition comprising debacarb and carbendazmin.

2. The method of using tilapia skin according to claim 1, wherein the process of producing tilapia skin further comprises the steps of:

removing the tilapia skins from the solution with at least 50% glycerol, saline, and 1% of a solution containing penicillin, streptomycin, and a fungicide composition comprising debacarb and carbendazmin before 24 hours have elapsed, washing the tilapia skins with a sterile saline solution and placing the tilapia skins in a sterile and hermetic container containing about 75% glycerol, 24% saline and 1% of a solution with penicillin, streptomycin and fungicide composition comprising debacarb and carbendazim, massaging the tilapia skins for 5 minutes in this solution, soaking the tilapia skins for 3 hours in a water bath centrifuge with a stirrer at a constant speed of about 15 revolutions per minute and a temperature of about 37° C.;

removing the tilapia skins, and rinsing them with sterile saline and placing the tilapia skins in a sterile and hermetic container containing about 99% glycerol, and 1% of a solution with penicillin, streptomycin and fungicide composition comprising debacarb and carbendazim, massaging the tilapia skins for 5 minutes in this solution and soaking the tilapia skins in a water bath centrifuge at a temperature of about 37° C. and about 15 revolutions per minute for about 3 hours, packaging the tilapia skins in sterile double plastic envelopes, and storing at about 4° C.

3. The method of using tilapia skin according to claim 1, wherein the process of producing tilapia skin further comprises the step of performing a bacterial count of the tilapia skin and performing a supplementary sterilization step if the bacterial count in the tilapia skin is above 10/3.

4. The method of using tilapia skin according to claim 3, wherein the supplementary sterilization step is a radio-sterilization step, with load dosages ranging from 15 to 50 Kilograys.

* * * * *